United States Patent
Bahadur et al.

[11] Patent Number: 6,069,185
[45] Date of Patent: May 30, 2000

[54] RADIATION CURABLE COMPOSITIONS CONTAINING ALKENYL ETHER FUNCTIONAL POLYISOBUTYLENES

[75] Inventors: Maneesh Bahadur; Toshio Suzuki, both of Midland, Mich.

[73] Assignees: Dow Corning Asia, Ltd., Tokyo, Japan; Dow Corning Corporation, Midland, Mich.

[21] Appl. No.: 09/199,261

[22] Filed: Nov. 25, 1998

[51] Int. Cl.[7] .................. C08J 3/28; C08J 7/18; C08F 2/48

[52] U.S. Cl. .................. 522/25; 522/18; 522/17; 522/148; 522/172; 427/489; 427/508

[58] Field of Search .................. 522/148, 172, 522/18, 25, 17; 427/489, 508

[56] References Cited

U.S. PATENT DOCUMENTS

| | | | |
|---|---|---|---|
| 4,617,238 | 10/1986 | Crivello et al. | 428/452 |
| 4,808,664 | 2/1989 | Saam | 525/106 |
| 4,904,732 | 2/1990 | Iwahara et al. | 525/100 |
| 5,270,423 | 12/1993 | Brown et al. | 528/15 |
| 5,594,042 | 1/1997 | Glover et al. | 522/31 |
| 5,629,095 | 5/1997 | Bujanowski et al. | 428/447 |
| 5,665,823 | 9/1997 | Saxena et al. | 525/106 |

FOREIGN PATENT DOCUMENTS

| | | |
|---|---|---|
| 462389 | 7/1991 | European Pat. Off. . |
| 562922 | 3/1993 | European Pat. Off. . |
| WO 9104992 | 11/1989 | WIPO . |
| WO 9211295 | 12/1991 | WIPO . |

OTHER PUBLICATIONS

Blyler et al. "Polymers for Coating Optical Fibers," Chemtech, 1987, pp. 680–684.
Hitchcock et al. "Agnew. Chem. Int. Ed. Engl.," 1991, pp. 438–440.
Liao et al. "Polymer Bulletin." V. 6, 1981, pp. 135–141.
Kennedy et al. "Polymeric Materials Science and Engineering." V. 58, 1998, p. 866.
Kennedy et al. "Journal of Polymer Science: Part A: Polymer Chemistry." V. 28, 190, p. 89.
Merrill et al. "RadTech North America Proceedings." V. 1, 1992, pp. 77–85.

*Primary Examiner*—Robert Dawson
*Assistant Examiner*—Kuo-Liang Peng
*Attorney, Agent, or Firm*—Timothy J. Troy

[57] ABSTRACT

This invention relates to radiation curable compositions comprising an alkenyl ether functional polyisobutylene, a cationic photoinitiator, a free radical photoinitiator, and an alkenyl ether compound which is free of isobutylene units. The radiation curable compositions can further comprise an alkylphenol. This invention also relates to hydrocarbon silicone alkenyl ether compounds. The radiation curable compositions exhibit a low cure energy, have a high moisture vapor barrier, high damping characteristics, and a high refractive index, and provide a barrier to corrosive vapors and have maintained or enhanced modulus, tensile strength, and toughness.

31 Claims, No Drawings

RADIATION CURABLE COMPOSITIONS CONTAINING ALKENYL ETHER FUNCTIONAL POLYISOBUTYLENES

FIELD OF THE INVENTION

This invention relates to radiation curable compositions. More particularly, this invention relates to radiation curable compositions comprising an alkenyl ether functional polyisobutylene, a cationic photoinitiator, a free radical photoinitiator, and optionally an alkenyl ether compound which is free of isobutylene units. The radiation curable compositions can also further comprise an alkylphenol.

BACKGROUND OF THE INVENTION

Polyisobutylenes containing functional groups which are radiation curable have been disclosed in the art. For example, T. P. Liao and J. P. Kennedy in *Polymer Bulletin*, V. 6, pp. 135–141 (1981) disclose acryl and methacryl telechelic polyisobutylenes having the formula $CH_2=C(R)$—COO-PIB—OOC—$C(R)=CH_2$ where R is —H or $CH_3$. These materials were prepared by reacting alpha, omega di-hydroxypolyisobutylene, $HOCH_2$-PIB—$CH_2OH$, and excess acryloyl or methacryloyl chloride. These prepolymers are disclosed as being useful in the synthesis of a variety of new composites containing a soft polyisobutylene segment.

J. P. Kennedy and B. Ivan in *Polymer Material Science and Engineering*, V. 58, p.866 (1988) disclose allyl telechelic linear and star-branched polyisobutylenes prepared by a convenient rapid one pot polymerization functionalization process. The polymerization step involved living polymerization of isobutylene by recently discovered mono- or multifunctional initiating systems (combinations of tert.-ester and ether/Lewis to acids) followed by electrophilic functionalizations by allyl trimethylsilane in the presence of TiC14. Characterization indicated quantitative end allylations. Subsequent quantitative derivations of the allyl termini yielded mono-, di-, and tri-functional hydroxyl- and epoxy-telechelic polyisobutylenes which could be cured to rubbery networks.

J. P. Kennedy and B. Ivan in the *Journal of Polymer Science, Part A, Polymer Chemistry*, V. 28, p. 89 (1990) disclose mono-, di-ended linear, and three-arm star allyl telechelic polyisobutylenes which are prepared by a rapid economical one-pot polymerization-functionalization process. The process involved the living polymerization of isobutylene by mono-, di-, or tri-functional initiating systems, specifically by aliphatic and aromatic tert-ester and -ether/$TiCl_4$ combinations, followed by electrophilic functionalization of the living sites with allyl-trimethylsilane. Quantitative derivations of the ally termini yielded mono-, di-, and tri-epoxy and -hydroxy-telechelic polyisobutylenes. It is further disclosed that strong rubbery networks were made by curing the epoxy-telechelic polyisobutylenes with triethylene tetramine and by reacting the hydroxy-telechelic polyisobutylenes with MDI.

N. A. Merrill, I. J. Gardner, and V. L. Hughes in RadTech North America Proceedings, V. 1, pp. 77–85 (1992) disclose conjugated diene functional polyisobutylenes which have a high reactivity to both ultraviolet and electron beam radiation. These conjugated diene functional polyisobutylenes, alone or in a formulation, are disclosed as being useful in preparing pressure sensitive adhesives.

In PCT Patent Publication No. WO 9104992 is disclosed a functionalized copolymer of isobutylene and a para-methylstyrene, wherein at least one type of functional group is attached to the para-methyl group of the para-methylstyrene, the copolymer having a substantially homogenous compositional distribution. The functionalized groups are exemplified by alkoxides, phenoxides, carboxylates, thiolates, thiopenolates, thioethers, thiocarboxylates, dithiocarboxylates, thioureas, dithiocarbamates, xanthanates, thiocyanates, silanes, halosilanes, malonates, cyanides, amides, amines, carbazoles, phthalimides, pyridine, maleimide, cyanates, and phosphines.

In PCT Patent Publication No. WO 9211295 is disclosed a radiation reactive functionalized polymer comprising an isoolefin having about 4 to about 7 carbon atoms and a para-alkylstyrene, wherein a radiation reactive functional group is attached to the para-alkyl group of the para-alkylstyrene, and discloses radiation curable pressure sensitive adhesives comprising the functionalized polymer and a tackifier. In WO'295, the radiation curable groups are disclosed as being groups such as thioxanthones, acrylates, aldehydes, ketones, and esters.

Saxena et al. in U.S. Pat. No. 5,665,823 disclose a method for preparing an acrylic functional polyisobutylene polymer or copolymer, the method comprising reacting a polyisobutylene polymer or copolymer which contains at least one carbon-bonded silanol group in it molecule with a silane having both an acrylic-containing group and a silicon-bonded hydrolyzable group in its molecule.

Furthermore, radiation curable compositions which contain vinyl ether functional organosilicon compounds have also been described in the art. For example, Crivello in U.S. Pat. No. 4,617,238 discloses a photopolymerizable composition comprising (a) an organopolysiloxane having at least one Si-bonded vinyloxy functional group of the formula $H_2C=CH$—O—G—, where G is alkylene (such as propylene) or alkylene interrupted by at least one divalent heteroradical selected from —O—, divalent phenylene, or substituted divalent phenylene, or combination of such heteroradicals, and (b) an onium salt catalyst. The '238 patent also describes a method wherein the vinyl ether group is introduced into the organopolysiloxane by addition (hydrosilylation) of compounds with an allyl and a vinyl ether group to an SiH group of the organopolysiloxane in the presence of a platinum catalyst. In the method of the '238 patent, only the allyl group is added to the SiH group while the vinyl ether group is preserved and thus only one vinyl ether group for each SiH group can be incorporated into the siloxane molecule at any given time.

European Patent Publication No. 0462389 teaches thermosetting organopolysiloxanes with oxyalkylene vinyl ether groups bonded by SiOC groups and the vinyl groups may be substituted by alkyl groups. EPO'389 also teaches a method for the preparation of these compounds and their application as photochemically thermosetting polysiloxanes in encapsulating compounds, as non-stick coating compounds for flat carriers or as modified additives in compounds which can be thermoset radically, cationically or by UV or electron radiation.

Brown et al., in U.S. Pat. No. 5,270,423 disclose organosilicon compounds with a siloxane portion of the general formula —OR'OCH=CHR" linked via an SiOC bond wherein R' is a divalent hydrocarbon group and R" is hydrogen or an alkyl group which are useful in radiation curable compositions, in which they are mixed with an initiator. The compositions are particularly useful in UV radiation curable coatings.

Glover et al. in U.S. Pat. No. 5,594,042 discloses radiation curable compositions comprising vinyl ether functional siloxanes and aromatic iodonium salt or aromatic sulfonium salt photoinitiators which cure upon exposure to ultraviolet or electron beam radiation. The vinyl ether groups are linked to the silicon atom on the siloxane through an SiOC bond and the photoinitiators are disclosed as being preferably either diaryliodonium salts of sulfonic acids or triarylsulfonium salts of sulfonic acids.

Bujanowski et al. in U.S. Pat. No. 5,629,095 disclose vinyl ether functional siloxane resins, radiation curable coating compositions comprising a vinyl ether functional siloxane resin and a photocleavable acid, and a coated article obtained by applying the radiation curable coating composition to a substrate and then exposing the coating to radiation in an amount sufficient to cure the coating. In the '095 patent, the vinyl ether group in the siloxane resin is attached to the silicone atom through an SiOC bond.

SUMMARY OF THE INVENTION

The present invention relates to radiation curable compositions comprising an alkenyl ether functional polyisobutylene, a cationic photoinitiator, a free radical photoinitiator, and optionally an alkenyl ether compound which is free of isobutylene units. The radiation curable compositions can also further comprise an alkylphenol.

This invention also relates to hydrocarbon silicone alkenyl ether compounds.

It is an object of this invention to produce radiation curable compositions which exhibit a low cure energy.

It is an object of this invention to produce radiation curable compositions which have a high moisture vapor barrier, high damping characteristics, and a high refractive index. It is an object of this invention to produce radiation curable compositions which provide a barrier to corrosive vapors and have maintained or enhanced modulus, tensile strength, and toughness.

DETAILED DESCRIPTION OF THE INVENTION

This invention relates to a radiation curable composition comprising: (A) an alkenyl ether-functional polyisobutylene polymer in which at least 50 mole percent of the non-terminal repeating units of the polymer are isobutylene units and containing at least one group having the formula

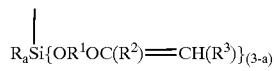

wherein R is independently selected from the group consisting of monovalent hydrocarbon groups and alkoxy groups, $R^1$ is a divalent hydrocarbon group having from 2 to 20 carbon atoms, $R^2$ and $R^3$ are independently selected from the group consisting of a hydrogen atom and a monovalent hydrocarbon group, and a has a value of 0 to 2, (B) a cationic photoinitiator, and (C) a free radical photoinitiator.

The monovalent hydrocarbon groups of R are exemplified by alkyl groups such as methyl, ethyl, propyl, butyl, hexyl, octyl, and decyl, aryl groups such as phenyl, tolyl, and xylyl, and can also be any monovalent hydrocarbon group which has at least one of its hydrogen atoms replaced with a halogen, such as fluorine, chlorine, or bromine, and these monovalent hydrocarbon groups are exemplified by $CF_3CH_2CH_2$— and $C_4F_9CH_2CH_2$—. The alkoxy groups are exemplified by methoxy, ethoxy, propoxy, and butoxy. It is highly preferred that R is independently selected from the group consisting of methyl and methoxy. Each R group can be the same or different, as desired.

Divalent hydrocarbon groups suitable as $R^1$ are exemplified by alkylene groups such as ethylene, propylene, butylene, pentylene, trimethylene, 2-methyltrimethylene, pentamethylene, hexamethylene, 3-ethyl-hexamethylene, octamethylene, decamethylene, —$(CH_2)_{18}$—, and cycloalkylene groups such as cyclohexylene, arylene groups such as phenylene. Examples of suitable divalent halohydrocarbon groups also include any divalent hydrocarbon group wherein one or more hydrogen atoms have been replaced by halogen, such as fluorine, chlorine or bromine exemplified by —$CH_2CH_2CF_2CF_2CH_2CH_2$—. Each $R^1$ can be the same or different as desired. Preferably $R^1$ is butylene.

The groups $R^2$ and $R^3$ are independently selected from a group consisting of a hydrogen atom and a monovalent hydrocarbon group exemplified by alkyl groups such as methyl, ethyl, propyl, butyl. The groups $R^2$ and $R^3$ may be the same or different. Preferably $R^2$ and $R^3$ are hydrogen atoms. In the formula above, it is preferred that a have a value of zero.

For the purposes of this invention, the backbone of the alkenyl ether functional polyisobutylene polymer may be any linear or branched polymer or copolymer wherein at least about 50 mole percent, preferably at least 80 mole percent, of the repeat units are isobutylene units having the following structure:

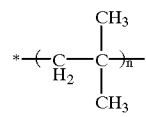

In the polymer or copolymer of the invention, the above described alkenyl ether group can be disposed either along the chain or at the terminals thereof, or any combination of the above. As used herein, the term "polymer" is generic to polymers, oligomers, and copolymers, all of which are within the scope of this invention.

In a preferred embodiment of this invention, the alkenyl ether functional polyisobutylene polymer (A) is a polymer containing at least one group having the formula

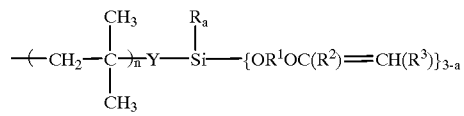

wherein at least 50 mole percent of the non-terminal repeating units of the polymer are isobutylene units, R is independently selected from the group consisting of monovalent hydrocarbon groups and alkoxy groups, $R^1$ is a divalent hydrocarbon group having from 2 to 20 carbon atoms, $R^2$ and $R^3$ are independently selected from group consisting of a hydrogen atom and a monovalent hydrocarbon group, n has a value from 5 to 10,000, a has a value of 0 to 2, and Y is selected from the group consisting of (i) an alkylene group having from 2 to 10 carbon atoms and (ii) a group having the formula

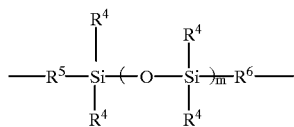

wherein $R^4$ is a monovalent hydrocarbon group, $R^5$ and $R^6$ are independently alkylene groups having from 2 to 10 carbon atoms, and m is an integer having a value from 1 to 5.

The groups R and $R^1$ are as defined hereinabove, including preferred embodiments thereof. Preferably, R is independently selected from the group consisting of methyl and methoxy, and $R^1$ is butylene. Preferably, a has a value of 0 or 1.

The alkylene groups of Y(i) are exemplified by ethylene, propylene, butylene, pentylene, trimethylene, 2-methyltrimethylene, pentamethylene, hexamethylene, 3-ethyl-hexamethylene, octamethylene, and decamethylene.

In the formula for Y(ii) above, the monovalent hydrocarbon groups of $R^4$ are as described above for R, and preferably $R^4$ is methyl. The alkylene groups for $R^5$ and $R^6$ are as defined above for Y(i). Preferably, $R^5$ and $R^6$ are independently selected from the group consisting of ethylene and propylene. It is highly preferred that $R^5$ is propylene, and $R^6$ is ethylene. It is also preferred that m has a value of 1.

It is preferred for purposes of this invention that from 10 to 100 weight percent of the alkenyl ether functional polyisobutylene polymer described above be used, and it is highly preferred that from 50 to 100 weight percent of this compound be employed, said weight percent being based on the total weight of the radiation curable composition.

Component (B) in the composition of this invention is cationic photoinitiator. Suitable cationic photoinitiators are selected from the group consisting of onium salts, diaryliodonium salts of sulfonic acids, triarylsulfonium salts of sulfonic acids, diaryliodonium salts of boronic acids, and triarylsulfonium salts of boronic acids.

The onium salts are preferably selected from the group consisting of $R^7_2I^+MX_z^-$, $R^7_3S^+MX_z^-$, $R^7_3Se^+MX_z^-$, $R^7_4P^+MX_z^-$, and $R^7_4N^+MX_z^-$, wherein each $R^7$ is an organic group having from 1 to 30 carbon atoms exemplified by aromatic carbocyclic groups having from 6 to 20 carbon atoms. Each $R^7$ can be substituted with from 1 to 4 monovalent hydrocarbon groups exemplified by alkoxy groups having from 1 to 8 carbon atoms, alkyl groups having from 1 to 16 carbon atoms, nitro, chloro, bromo, cyano, carboxyl, mercapto, and aromatic heterocyclic groups exemplified by pyridyl, thiophenyl, and pyranyl. The symbol M in the formulae hereinabove are metals or metalloids which include transition metals exemplified by Sb, Fe, Sn, Bi, Al, Ga, In, Ti, Zr, Sc, V, Cr, Mn, Cs, rare earth metals exemplified by lanthanides, for example, Cd, Pr, and Nd, and metalloids exemplified by B, P, and As. $MX_z^-$ is a non-basic, non-nucleophilic anion exemplified by $BF_4^-$, $PF_6^-$, $AsF_6^-$, $SbF_6^-$, $SbCl_6^-$, $HSO_4^-$, $ClO_4^-$, $FeCl_4=$, $SnCl_6^-$, and $BiCl_5=$.

Preferred onium salts are exemplified by bis-diaryl iodonium salts, for example, bis(dodecyl phenyl) iodonium hexafluoroarsenate, bis(dodecylphenyl) iodonium hexafluoroantimonate, and dialkylphenyl iodonium hexafluoroantimonate.

Diaryliodonium salts of sulfonic acids, triarylsulfonium salts of sulfonic acids, diaryliodonium salts of boronic acids, and triarylsulfonium salts of boronic acids are also suitable as the cationic photoinitiator (B). Preferred diaryliodonium salts of sulfonic acid are diaryliodonium salts of perfluoroalkylsulfonic acids and diaryliodonium salts of aryl sulfonic acids. Preferred diaryliodonium salts of perfluoroalkylsulfonic acids are exemplified by diaryliodonium salts of perfluorobutanesulfonic acid, diaryliodonium salts of perfluoroethanesulfonic acid, diaryliodonium salts of perfluoro-octanesulfonic acid, and diaryliodonium salts of trifluoromethane sulfonic acid. Preferred diaryliodonium salts of aryl sulfonic acids are exemplified by diaryliodonium salts of para-toluene sulfonic acid, diaryliodonium salts of dodecylbenzene sulfonic acid, diaryliodonium salts of benzene sulfonic acid, and diaryliodonium salts of 3-nitrobenzene sulfonic acid.

Preferred triarylsulfonium salts of sulfonic acid are triarylsulfonium salts of perfluoroalkylsulfonic acids and triarylsulfonium salts of aryl sulfonic acids. Preferred triarylsulfonium salts of perfluoroalkylsulfonic acids are exemplified by triarylsulfonium salts of perfluorobutanesulfonic acid, triarylsulfonium salts of perfluoroethanesulfonic acid, triarylsulfonium salts of perfluoro-octanesulfonic acid, and triarylsulfonium salts of trifluoromethane sulfonic acid. Preferred triarylsulfonium salts of aryl sulfonic acids are exemplified by triarylsulfonium salts of para-toluene sulfonic acid, triarylsulfonium salts of dodecylbenzene sulfonic acid, triarylsulfonium salts of benzene sulfonic acid, and triarylsulfonium salts of 3-nitrobenzene sulfonic acid.

Preferred diaryliodonium salts of boronic acids, and triarylsulfonium salts of boronic acids are compounds such as those disclosed in European Patent Application No. 0562922. Preferred diaryliodonium salts of boronic acids include diaryliodonium salts of perhaloarylboronic acids and preferred triarylsulfonium salts of boronic acids are the triarylsulfonium salts of perhaloarylboronic acid.

Preferably the amount of cationic photoinitiator (B) is from 0.01 to 5.0 weight percent based on the total weight of the composition, and it is highly preferred to use from 0.1 to 2.0 weight percent based on the total weight of the radiation curable composition.

Component (C) in the compositions of this invention is a free radical photoinitiator. The free radical photoinitiators of this invention can be any benzoins exemplified by benzoin alkyl ethers, benzophenone and its derivatives such as 4,4'-dimethyl-amino-benzophenone (Michler's Ketone), acetophenones exemplified by dialkoxyacetophenones, dichloroacetophenones, and trichloroacetophenones, benzils exemplfied by benzil ketals, quinones, and O-acylated -α-oximinoketones. Preferably the free radical photoinitiator is a compound having the formula

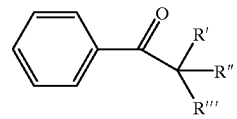

wherein R' is selected from the group consisting of —H, an alkoxy group, and a halogen atom, R" is selected from the group consisting of —OH, an alkoxy group, and a halogen atom, and R'" is selected from the group consisting of —H, an alkyl group, and a halogen atom. Preferred embodiments of this compound are (i) where R' is —H, R" is —OH and R'" is methyl or phenyl, (ii) where R' is —H, R" is an alkoxy group and R'" is phenyl (for benzoin alkyl ethers), (iii) where both R' and R" are alkoxy groups and R'" is phenyl (for benzil ketals), (iv) where both R' and R" are alkoxy groups and R'" is —H (for dialkoxyacetophenones), and (v) where both R' and R" are —Cl and R'" is —Cl or —H (for di- and tri- chloroacetophenones). It is especially preferred for the compositions that component (C) is Darocur® 1173 (2-hydroxy-2-methyl-1-phenyl-propan-1-one).

Preferably the amount of free radical photoinitiator (C) is from 0.01 to 5.0 weight percent based on the total weight of the composition, and it is highly preferred to use from 0.1 to 2.0 weight percent based on the total weight of the radiation curable composition.

The compositions of this invention can further comprise (D) an alkenyl ether compound which is free of isobutylene units. Component (D) is exemplified by alkenyl ether compounds selected from the group consisting of (i) a vinyl ether compound having the formula $(CH_2=CHOR^8)_d CR^9_{4-d}$ wherein $R^8$ is a divalent hydrocarbon group having from 1 to 20 carbon atoms, $R^9$ is selected from the group consisting of hydrogen and a monovalent hydrocarbon group having from 1 to 20 carbon atoms, and d has a value of 1 to 3, (ii) a hydrocarbon silicone alkenyl ether compound having the formula

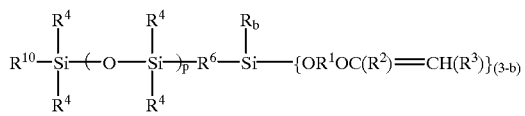

wherein $R^1$ and $R^6$ are independently divalent hydrocarbon groups having from 1 to 20 carbon atoms, $R^4$ is a monovalent hydrocarbon group having from 1 to 20 carbon atoms, $R^2$ and $R^3$ are independently selected from group consisting of a hydrogen atom and a monovalent hydrocarbon group, $R^{10}$ is an alkyl group having from 8 to 16 carbon atoms, R is independently selected from the group consisting of $R^4$ and an alkoxy group, b has a value of 0 to 2, and p has a value of 0 to 1, and (iii) a long chain hydrocarbon silicone alkenyl ether compound having the formula

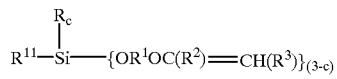

wherein R is independently selected from a group consisting of monovalent hydrocarbons having from 1 to 20 carbon atoms and an alkoxy group, $R^{11}$ is an alkyl group having from 8 to 16 carbon atoms, $R^2$ and $R^3$ are independently selected from a group consisting of a hydrogen atom and a monovalent hydrocarbon groups, $R^1$ is a divalent hydrocarbon group having 1 to 20 carbon atom, and c has a value of 0 to 2.

The monovalent and divalent hydrocarbon groups are as delineated above for the alkenyl ether functional polyisobutylene, including preferred embodiments thereof. In the formula for (i), preferably $R^8$ is an alkylene group having from 1 to 6 carbon atoms, preferably methylene, $R^9$ is an alkyl group having from 1 to 10 carbon atoms, preferably ethyl, and d has a value of 3.

In the formula for (ii), preferably $R^1$ and $R^6$ are independently alkylene groups having from 1 to 6 carbon atoms, preferably $R^1$ is butylene and $R^6$ is ethylene, $R^4$ is an alkyl group having from 1 to 10 carbon atoms, preferably methyl, $R^{10}$ is exemplified by octyl ($-C_8H_{17}$), decyl ($-C_{10}H_{21}$), dodecyl ($-C_{12}H_{25}$), tetradecyl ($-C_{14}H_{29}$), and hexadecyl ($-C_{16}H_{33}$), with dodecyl and hexadecyl being preferred, $R^2$ and $R^3$ are independently selected from a group consisting of a hydrogen atom and a monovalent hydrocarbon group, preferably $R^2$ and $R^3$ are each hydrogen atoms, R is independently selected from the group consisting of methyl and methoxy, preferably b has a value of 0, and preferably p has a value of 0 or 1, preferably 1.

In the formula for (iii), preferably $R^1$ is an alkylene group having from 1 to 6 carbon atoms, preferably $R^1$ is butylene, R is independently selected from the group consisting of methyl and methoxy, $R^{11}$ is exemplified by dodecyl ($-C_{12}H_{25}$), tetradecyl ($-C_{14}H_{29}$), and hexadecyl ($-C_{16}H_{33}$), with dodecyl and hexadecyl being preferred, $R^2$ and $R^3$ are independently selected from group consisting of a hydrogen atom and a monovalent hydrocarbon group, preferably $R^2$ and $R^3$ are hydrogen atoms, and preferably c has a value of 0.

Preferably the amount of Component (D) is up to 70 weight percent based on the total weight of the composition, and it is highly preferred to use from 0 to 50 weight percent based on the total weight of the radiation curable composition.

The compositions of this invention can also further comprise (E) an alkylphenol having from 6 to 18 carbon atoms. The alkyl group is exemplified by hexyl ($-C_6H_{13}$), octyl ($-C_8H_{17}$), decyl ($-C_{10}H_{21}$), dodecyl ($-C_{12}H_{25}$), tetradecyl ($-C_{14}H_{29}$), hexadecyl ($-C_{16}H_{33}$), and octadecyl ($-C_{18}H_{37}$), with dodecyl being preferred. It is especially preferred that (E) is dodecylphenol. For the purposes of this invention, "dodecylphenol" denotes a compound having the formula $C_{12}H_{25}C_6H_4OH$ or a mixture comprising isomers of a compound having the formula $C_{12}H_{25}C_6H_4OH$.

Preferably the amount of dodecylphenol (E) is up to 5.0 parts by weight, and it is highly preferred to use from 0.5 to 2.0 parts by weight per 100 parts by weight of the radiation curable composition.

The radiation curable compositions of this invention can also contain ingredients exemplified by reinforcing and extending fillers such as treated silicas, hydrocarbon diluents such as linear alkyl dodecylbenzene and functional hydrocarbons such as $C_{8-16}$ aliphatic glycidyl ethers, sensitizers such as 2-isopropylthioxanthone or benzophenone, colorants, dyes, preservatives, fragrances, stabilizers and adhesion modifiers.

The radiation curable compositions of this invention can be prepared by mixing the materials described hereinabove and any optional components in any order, using any suitable mixing means, such as a spatula, a drum roller, a mechanical stirrer, a three-roll mill, a sigma blade mixer, a bread dough mixer, or a two-roll mill.

This invention further relates to a method of making a radiation curable composition comprising (I) mixing components (A)–(C) and optionally (D) described hereinabove. The method can further comprise (II) adding (E) an alkylphenol having from 6 to 18 carbon atoms during step (I). Components (A)–(E) are as described above, including preferred embodiments and amounts thereof.

The present invention further relates to a method of making an article of manufacture comprising (I) applying a radiation curable composition comprising components (A)–(C) described hereinabove, to a solid substrate to form a coating, and (II) exposing the coating to an energy source selected from the group consisting of (i) ultraviolet light and (ii) visible light in an amount sufficient to cure the coating.

The composition of (I) can further comprise (D) an alkenyl ether compound which is free of isobutylene units, and (E) an alkylphenol having from 6 to 18 carbon atoms, and any of the optional ingredients recited above. Components (A)–(E) and the optional ingredients are as described above, including preferred embodiments and amounts thereof.

The coating may be applied by any suitable manner known in the art, such as by spreading, brushing, extruding, spraying, gravure, kiss-roll and air-knife.

The solid substrate can be a flexible sheet material such as paper, polyolefin film, polyolefin-coated paper, foil, wood, cardboard and cotton, metallic materials such as aluminum, copper, steel and silver, siliceous materials such as glass and stone, and synthetic polymer materials such as polyolefins, polyamides, polyesters and polyacrylates. As to form, the solid substrate can be substantially sheet-like, such as a peelable release liner for pressure sensitive adhesive, a fabric or a foil, or a fiber, or a substantially three-dimensional in form.

Curing itself may be achieved in any of the known ways, including passing a coated substrate under the desired source of radiation, for example a UV lamp, at a predetermined rate and exposing a completely coated substrate to radiation by switching on the required energy source for a predetermined time.

The radiation curable compositions are preferably cured in the form of films. The cured films are expected to have high refractive index, good barrier properties, good adhesion and good damping properties. It is preferable to apply these coatings to surfaces that are adversely affected by exposure to oxygen, moisture vapor and other environmental factors. The radiation curable coatings are particularly useful as high refractive index coatings for optical fibers. The application of the radiation curable compositions to optical fibers and curing of the compositions can be achieved by conventional equipment (see Blyler and Aloisio Polymers for Coating Optical Fibers, Chemtech, November, 1987, pages 680–684). The curable compositions can also be used as an additive to compositions whose barrier properties needs to be tailored to higher values. The radiation curable compositions can be used to increase the barrier properties of sealants and pottants used for encapsulating electronic devices that are adversely affected by moisture.

This invention also relates to a hydrocarbon silicone alkenyl ether compound having the formula

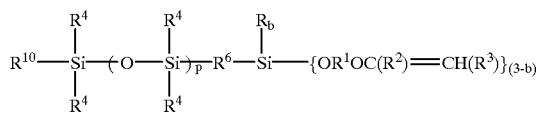

wherein $R^1$ and $R^6$ are divalent hydrocarbon groups having from 1 to 20 carbon atoms, $R^4$ is a monovalent hydrocarbon group having from 1 to 20 carbon atoms, $R^{10}$ is an alkyl group having from 8 to 16 carbon atoms, $R^2$ and $R^3$ are independently selected from a group consisting of a hydrogen atom and a monovalent hydrocarbon group, R is independently selected from the group consisting of $R^4$ and an alkoxy group, b has a value of 0 to 2, and p has a value of 0 to 1.

Preferably $R^1$ and $R^6$ are alkylene groups having from 1 to 6 carbon atoms, preferably $R^1$ is butylene and $R^6$ is ethylene, $R^4$ is an alkyl group having from 1 to 10 carbon atoms, preferably methyl, $R^2$ and $R^3$ are independently selected from a group consisting of a hydrogen atom and a monovalent hydrocarbon groups, preferably $R^2$ and $R^3$ are each hydrogen atoms, $R^{10}$ is exemplified by octyl ($—C_8H_{17}$), decyl ($—C_{10}H_{21}$), dodecyl ($—C_{12}H_{25}$), tetradecyl ($—C_{14}H_{29}$), and hexadecyl ($—C_{16}H_{33}$), with dodecyl and hexadecyl being preferred, R is independently selected from the group consisting of methyl and methoxy, preferably b has a value of 0, and preferably p has a value of 0 or 1, preferably 1.

This invention also relates to a hydrocarbon silicone alkenyl ether compound having the formula

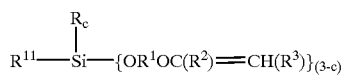

wherein R is independently selected from a group consisting of monovalent hydrocarbon group having from 1 to 20 carbon atoms and an alkoxy group, $R^2$ and $R^3$ are independently selected from group consisting of a hydrogen atom and a monovalent hydrocarbon group, $R^{11}$ is an alkyl group having from 8 to 16 carbon atoms, $R^1$ is a divalent hydrocarbon group having 1 to 20 carbon atom and c has a value of 0 to 2.

Preferably $R^1$ is an alkylene group having from 1 to 6 carbon atoms, preferably $R^1$ is butylene, $R^2$ and $R^3$ are independently selected from group consisting of a hydrogen atom and a monovalent hydrocarbon groups, preferably $R^2$ and $R^3$ are each hydrogen atoms, R is independently selected from the group consisting of methyl and methoxy. $R^{11}$ is exemplified by dodecyl ($—C_{12}H_{25}$), tetradecyl ($—C_{14}H_{29}$), and hexadecyl ($—C_{16}H_{33}$), with dodecyl and hexadecyl being preferred, preferably c has a value of 0.

EXAMPLES

Materials

The allyl functional polyisobutylene (PIB) polymer was made by Kaneka Corporation and is called Epion™ 200A polymer. Hydroxybutyl vinyl ether, 1-hexadecene, methyltrichlorosilane and methyldichlorosilane was purchased from Aldrich Chemical Company, as were other solvents and common reagents used in the examples. Trimethylolpropane trivinyl ether was obtained from BASF Corporation. The platinum (vinylsiloxane) catalyst was prepared by the procedure of Hitchcock et. al., Angew. Chem. Int. Ed. Engl. 1991, 30. $^{13}C$ and $^{29}Si$ nuclear magnetic resonance spectroscopy was used to confirm the structures. Molecular weight of each polyisobutylene was determined by gel permeation chromatography using PIB standards.

Cure Studies

The formulations were mixed in a Hauschild mixer by placing the desired amounts of components as noted in the examples. The cure study was performed on either a Fusion curing processor (300 or 600 watt lamps) or differential photocalorimeter (DPC) equipment. In the Fusion curing processor, the coating was applied on to a glass slide and by a roll coater or manually. The glass slide was conveyed through the Fusion curing processor at a fixed line speed, and cure energy was controlled by adjusting belt speeds. An IL 1350 radiometer/photometer (from International Lights) was used to monitor the ultraviolet light flux at the sample. The extent of cure was measured by observing surface tack (dry to touch) immediately after ultraviolet light curing. Through cure was evaluated by removing the cured film from substrate and evaluating tack at the bottom. Film thickness was measured by a micrometer. The DPC studies were conducted on a 930 model DPC (DuPont Instruments) and a model 910 differential scanning calorimeter (DuPont Instruments) equipped with a Fusion 300 watt Lamp. All DPC measurements were made in air. In all cases a radiometer was used to obtain the cure energy. Samples were radiated in-situ at 25° C. in air. The DPC data was analyzed using V4.1A DuPont 21000 software. DPC induction times were measured from first exposure to 1% conversion.

Example 1

Production of the methoxysilyl functional polyisobutylene Polymer

The methoxysilyl-functional polyisobutylene polymers were prepared per the procedure disclosed by Saam et. al. in Example 2 of U.S. Pat. No. 4,808,664, except that the starting polyisobutylene polymer was the commercially available Epion™ 200A (an allyl telechelic polyisobutylene made by Kaneka Corporation, Tokyo, Japan).

Example 2

A mixture of 1112 g of the polymer from example 1 and 1500 ml of cyclohexane was added to a round bottom flask, equipped with mechanical stirrer, Dean-Stark separator, and reflux condenser. To the flask was added 140 grams of 4-hydroxybutyl vinyl ether (HO(CH$_2$)$_4$OCH=CH$_2$) and 0.5 ml of tetraisopropyl titanate. The reaction mixture was heated at a temperature of 70° C. with stirring for eight hours, during which time approximately 35 ml of methanol was removed from the Dean-Stark separator. Proton nuclear magnetic resonance spectrum of a small sample confirmed that the product had the following structure:

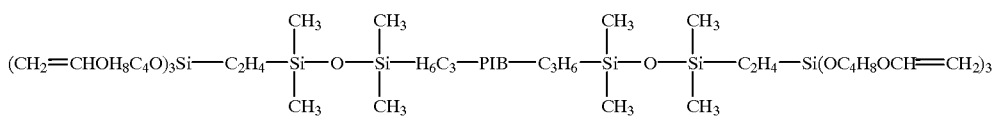

(Note: PIB denotes the initial polyisobutylene polymer)

The cyclohexane solvent was removed with a thin film stripper. Molecular weight data: M$_n$=6800; M$_w$ 10400; M$_w$/M$_n$=1.52. This polymer is hereinafter referred to as POLYMER A.

Example 3

50 grams of Epion™ 200A was dissolved 150 ml of heptane. Platinum (vinylsiloxane) catalyst was added to the mixture at a molar ratio of 1×10$^{-4}$ equivalents/allyl group, and 1.10 (equivalents per allyl group) of trichlorosilane was added dropwise to the reaction mixture. The reaction mixture was maintained for eight hours at 70° C. Proton nuclear magnetic resonance spectra confirmed the absence of allyl resonance's. After cooling to room temperature 40 ml of methylene chloride was added to the flask followed by 15 g of triethylamine. Thereafter, 15 ml of 4-hydroxybutyl vinyl ether was added dropwise from an addition funnel to the flask and after addition the contents were allowed to stir overnight. The precipitated salts were filtered off. The polymer was isolated by precipitation into methanol and dried. Proton nuclear magnetic resonance spectra of the product confirms the following structure:

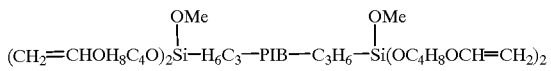

Molecular Weight data: M$_n$=7528, M$_w$=35420; M$_w$/M$_n$= 4.70.
This polymer is hereinafter referred to as POLYMER B.

Example 4

150 g of 1-hexadecene, 250 ml of cyclohexane and platinum (vinylsiloxane) catalyst at a molar ratio of 1×10$^{-5}$ (equivalents/ C=C) were added to a round bottom flask equipped with a magnetic stirrer, reflux condenser, addition funnel and thermometer. Next, 186 grams of a siloxane having the formula

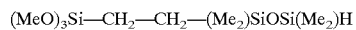

(disclosed in U.S. Pat. No. 4,808,664), wherein Me hereinafter denotes a methyl group, was added slowly over a period of 30 minutes. The reaction was continued for 70° C. for two hours. GC analysis showed complete conversion. The reactor was evacuated (20 mm Hg) to strip off excess olefins. At this time 235 g of 4-hydroxybutyl vinyl ether and Tyzor® TPT catalyst (from Dupont) at a molar ratio of 5×10$^{-4}$ (equivalents/ C=C) were added to the pot and a Dean stark separator was added to the apparatus. After 5–6 hours of reflux approximately 60 ml of methanol was recovered from dean-stark separator. GC analysis showed approximately 90% conversion. Proton NMR data indicated the following structure:

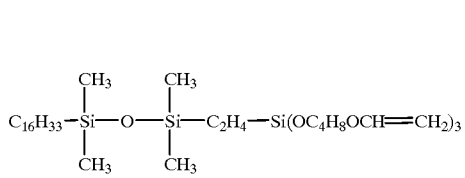

This sample is referred to as Liquid A.

Example 5

Three formulations containing polymer A, liquid A, a 60/40 weight to weight mixture of tolyl (dodecylphenyl) iodonium trifluoromethanesulfonate diluted in dodecylphenol (hereinafter denoted "triflate catalyst"), a cationic photoinitiator, and Darocur® 1173 (2-hydroxy-2-methyl-1-phenyl-propan-1-one from Ciba Geigy, Terrytown, N.Y.), a free radical photoinitiator, were prepared by mixing these ingredients together in the amounts shown in Table 1.

TABLE 1

| Sample | Liquid A (wt %) | Polymer A (wt %) | Triflate catalyst (wt %) | Darocur ® 1173 (wt %) |
|---|---|---|---|---|
| A | 38 | 60 | 2 | — |
| B | 38 | 58 | 4 | — |
| C | 38 | 58 | 2 | 2 |

The samples were tested in a DPC apparatus at 25° C. in air at 1.10 (Joules/cm$^2$) cure energy. The analysis results of the DPC exotherm is reported in Table 2 below.

TABLE 2

| Sample | Cure Energy (J/cm$^2$) | Cure Rate (W/g/min.) | Induction Time (s) | Peak Max. (s) | Thickness (mm) |
|---|---|---|---|---|---|
| A | 1.11 | 3.94 | 11 | 43 | 0.35 |
| B | 1.11 | 5.96 | 10 | 36 | 0.60 |
| C | 1.11 | 52.76 | 4 | 14 | 0.90 |

The results show faster cure rate for ultraviolet cure of Sample C which contained both a free radical photoinitiator (such as Darocur® 1173) and cationic photoinitiator (such as the triflate catalyst) as compared with those which contained a cationic photoinitiator alone in formulations A and B. It is to be noted that the free radical photoinitiator alone will not provide ultraviolet cure of the composition. The preferred catalyst combination reduces the amount of cationic photocatalyst required in the formulation with faster ultraviolet cure rates. The faster ultraviolet cure rates are not possible by increased amounts of the cationic photoinitiator alone.

Example 6

Three formulations containing polymer A, liquid A, Darocur® 1173 and a mixture of bis(4-dodecylphenyl) iodonium hexafluoroantimonate (30–60 weight percent), $C_{12-14}$ alkylglycidyl ethers (30–60 weight percent), linear alkylate dodecylbenzene (5–10 weight percent), 2-isopropylthioxanthone (1–5 weight percent) (hereinafter the mixture is denoted as "antimonate catalyst"), were prepared by mixing these ingredients together in the amounts shown in Table 3.

TABLE 3

| Sample | Liquid A (wt %) | Polymer A (wt %) | Antimonate catalyst (wt %) | Darocur® 1173 (wt %) |
|---|---|---|---|---|
| D | 38 | 60 | 2 | — |
| E | 38 | 58 | 4 | — |
| F | 38 | 58 | 2 | 2 |

The samples were tested in a DPC apparatus at 25° C. in air at 1.10 (Joules/cm$^2$) cure energy. The analysis results of the DPC exotherm is reported in Table 4 below.

TABLE 4

| Sample | Cure Energy (J/cm$^2$) | Cure Rate (W/g/min.) | Induction Time (s) | Peak Max. (s) | Thickness (mm) |
|---|---|---|---|---|---|
| D | 1.11 | 23.05 | 10 | 32 | 0.95 |
| E | 1.11 | 30.08 | 7 | 27 | 0.85 |
| F | 1.11 | 63.75 | 4 | 14 | 1.20 |

The DPC results for Sample F in Table 3 as compared to Samples D and E showed that Sample F had a faster reaction rate than Samples D and E.

Example 7

The following example shows that formulation of the composition can be varied to achieve a similar effect. In this formulation, the liquid A is replaced with trimethylolpropane trivinyl ether (TMPTVE) and Polymer A is replaced with the polymer B. The formulations and DPC results are shown in Tables 5 and 6.

TABLE 5

| Sample | Polymer B (wt %) | TMPTVE (wt %) | Triflate catalyst (wt %) | Darocur® 1173 (wt %) |
|---|---|---|---|---|
| G | 59.0 | 38.0 | 3.0 | — |
| H | 58.0 | 38.0 | 2.0 | 2.0 |

TABLE 6

| Sample | Cure Energy (mJ/cm$^2$) | Induction Time (s) | Enthalpy (J/g) | Peak Max. (s) |
|---|---|---|---|---|
| G | 620 | 6.2 | 145 | 20 |
| H | 100 | 4.4 | 180 | 18 |

At a lower cure energy of 100 mJ/cm$^2$, the DPC exotherm for formulation H is similar to the formulation G, a DPC exotherm at 620 mJ/cm$^2$. The mixed catalyst provides a faster UV cure rates.

Example 8

Formulations shown in Table 7 were coated onto glass slides at approximately 2–4 micron thickness. A cure study was performed on a Fusion curing processor (300 Watt lamps), at a fixed line speed, and cure energy was controlled by adjusting belt speeds. The minimum cure energy required for achieving a tack free surface was determined and the results are shown in Table 8.

TABLE 7

| Sample | Liquid A (wt %) | Polymer A (wt %) | Triflate catalyst (wt %) | Antimonate catalyst (wt %) | Darocur® 1173 (wt %) |
|---|---|---|---|---|---|
| I | 38 | 58 | 4 | — | — |
| J | 38 | 58 | 2 | — | 2 |
| K | 38 | 58 | — | 4 | — |
| L | 38 | 58 | — | 2 | 2 |

TABLE 8

| Sample | Cure Energy (mJ/cm$^2$) | Line speed (ft/min.) |
|---|---|---|
| I | 350 | 90 |
| J | 88 | 290 |
| K | 200 | 150 |
| L | 88 | 290 |

That which is claimed is:
1. A radiation curable composition comprising:
(A) an alkenyl ether-functional polyisobutylene polymer in which at least 50 mole percent of the non-terminal repeating units of the polymer are isobutylene units and containing at least one group having the formula

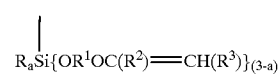

wherein R is independently selected from the group consisting of monovalent hydrocarbon groups and alkoxy groups, $R^1$ is a divalent hydrocarbon group having from 2 to 20 carbon atoms, $R^2$ and $R^3$ are independently selected from the group consisting of a hydrogen atom and a monovalent hydrocarbon group, and a has a value of 0 to 2;

(B) a cationic photoinitiator; and (C) a free radical photoinitiator.

2. A composition according to claim 1, wherein R is independently selected from the group consisting of methyl and methoxy, $R^1$ is butylene, $R^2$ and $R^3$ are hydrogen atoms, and a has a value of zero.

3. A composition according to claim 1, wherein (A) is a polymer containing at least one group having the formula

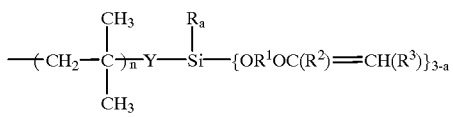

wherein at least 50 mole percent of the non-terminal repeating units of the polymer are isobutylene units, R is independently selected from the group consisting of monovalent hydrocarbon groups and alkoxy groups, $R^1$ is a divalent hydrocarbon group having from 2 to 20 carbon atoms, $R^2$ and $R^3$ are independently selected from group consisting of a hydrogen atom and a monovalent hydrocarbon group, n has a value from 5 to 10,000, a has a value of 0 to 2, and Y is selected from the group consisting of (i) an alkylene group having from 2 to 10 carbon atoms and (ii) a group having the formula

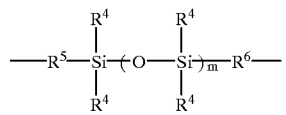

where $R^4$ is a monovalent hydrocarbon group, $R^5$ and $R^6$ are independently alkylene groups having from 2 to 10 carbon atoms, and m is an integer having a value from 1 to 5.

4. A composition according to claim 3, wherein R is independently selected from the group consisting of methyl and methoxy, $R^1$ is butylene, $R^2$ and $R^3$ are hydrogen atoms, a has a value of 0 or 1, and Y(i) is selected from the group consisting of ethylene, propylene, butylene, pentylene, trimethylene, 2-methyltrimethylene, pentamethylene, hexamethylene, 3-ethyl-hexamethylene, octamethylene, and decamethylene.

5. A composition according to claim 3, wherein R is independently selected from the group consisting of methyl and methoxy, $R^1$ is butylene, $R^2$ and $R^3$ are hydrogen atoms, and a has a value of 0 or 1, $R^4$ is methyl, $R^5$ is propylene, $R^6$ is ethylene, and m has a value of 1.

6. A composition according to claim 1, wherein (B) is selected from the group consisting of onium salts, diaryliodonium salts of sulfonic acids, triarylsulfonium salts of sulfonic acids, diaryliodonium salts of boronic acids, and triarylsulfonium salts of boronic acids.

7. A composition according to claim 1, wherein (B) is selected from the group consisting of bis(dodecyl phenyl) iodonium hexafluoroarsenate, bis(dodecylphenyl) iodonium hexafluoroantimonate, dialkylphenyl iodonium hexafluoroantimonate, diaryliodonium salts of perfluorobutanesulfonic acid, diaryliodonium salts of perfluoroethanesulfonic acid, diaryliodonium salts of perfluoro-octanesulfonic acid, diaryliodonium salts of trifluoromethane sulfonic acid, diaryliodonium salts of para-toluene sulfonic acid, diaryliodonium salts of dodecylbenzene sulfonic acid, diaryliodonium salts of benzene sulfonic acid, diaryliodonium salts of 3-nitrobenzene sulfonic acid, triarylsulfonium salts of perfluorobutanesulfonic acid, triarylsulfonium salts of perfluoroethanesulfonic acid, triarylsulfonium salts of perfluoro-octanesulfonic acid, triarylsulfonium salts of trifluoromethane sulfonic acid, triarylsulfonium salts of para-toluene sulfonic acid, triarylsulfonium salts of dodecylbenzene sulfonic acid, triarylsulfonium salts of benzene sulfonic acid, triarylsulfonium salts of 3-nitrobenzene sulfonic acid, diaryliodonium salts of perhaloarylboronic acids, and triarylsulfonium salts of perhaloarylboronic acid.

8. A composition according to claim 1, wherein (B) is selected from the group consisting of diaryliodonium salts of trifluoromethane sulfonic acid and triarylsulfonium salts of trifluoromethane sulfonic acid.

9. A composition according to claim 1, wherein (C) is a compound having the formula

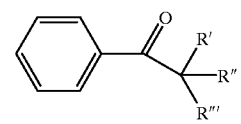

wherein R' is selected from the group consisting of —H, an alkoxy group, and a halogen atom, R" is selected from the group consisting of —OH, an alkoxy group, and a halogen atom, and R'" is selected from the group consisting of —H, an alkyl group, and a halogen atom.

10. A composition according to claim 1, wherein (C) is 2-hydroxy-2-methyl-1-phenyl-propan-1-one.

11. A composition according to claim 1, wherein the composition further comprises (D) an alkenyl ether compound which is free of isobutylene units.

12. A composition according to claim 11, wherein is (D) is selected from the group consisting of (i) a vinyl ether compound having the formula $(CH_2=CHOR^8)_d CR^9_{4-d}$ wherein $R^8$ is a divalent hydrocarbon group having from 1 to 20 carbon atoms, $R^9$ is selected from the group consisting of hydrogen and a monovalent hydrocarbon group having from 1 to 20 carbon atoms, and d has a value of 1 to 3, (ii) a hydrocarbon silicone alkenyl ether compound having the formula

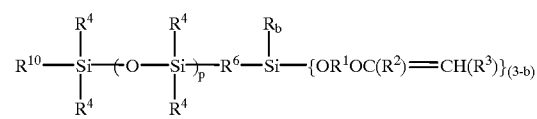

wherein $R^1$ and $R^6$ are independently divalent hydrocarbon groups having from 1 to 20 carbon atoms, $R^4$ is a monovalent hydrocarbon group having from 1 to 20 carbon atoms, $R^{10}$ is an alkyl group having from 8 to 16 carbon atoms, R is independently selected from the group consisting of $R^4$ and an alkoxy group, b has a value of 0 to 2, and p has a value of 0 to 1, and (iii) a long chain hydrocarbon silicone alkenyl ether compound having the formula

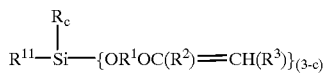

wherein R is independently selected from a group consisting of monovalent hydrocarbons having from 1 to 20 carbon atoms and an alkoxy group, $R^{11}$ is an alkyl group having from 8 to 16 carbon atoms, $R^2$ and $R^3$ are independently selected from a group consisting of a hydrogen atom and a monovalent hydrocarbon group, $R^1$ is a divalent hydrocarbon group having 1 to 20 carbon atom, and c has a value of 0 to 2.

13. A composition according to claim 12, wherein $R^8$ is methylene, $R^9$ is ethyl, and d has a value of 3.

14. A composition according to claim 12, wherein $R^1$ is butylene, $R^6$ is ethylene, $R^4$ methyl, $R^{10}$ is selected from the group consisting of dodecyl and hexadecyl, $R^2$ and $R^3$ are each hydrogen atoms, R is independently selected from the group consisting of methyl and methoxy, b has a value of 0, and p has a value of 1.

15. A composition according to claim 12, wherein $R^1$ is butylene, R is independently selected from the group consisting of methyl and methoxy, $R^{11}$ is selected from the group consisting of dodecyl and hexadecyl, $R^2$ and $R^3$ are each hydrogen atoms, and c has a value of 0.

16. A composition according to claim 1, wherein the composition further comprises (E) an alkylphenol having from 6 to 18 carbon atoms.

17. A composition according to claim 11, wherein the composition further comprises (E) an alkylphenol having from 6 to 18 carbon atoms.

18. A composition according to claim 12, wherein the composition further comprises (E) an alkylphenol having from 6 to 18 carbon atoms.

19. A composition according to claim 16, wherein (E) is dodecylphenol.

20. A composition according to claim 17, wherein (E) is dodecylphenol.

21. A composition according to claim 18, wherein (E) is dodecylphenol.

22. A method of making a radiation curable composition comprising:
(I) mixing
(A) an alkenyl ether-functional polyisobutylene polymer in which at least 50 mole percent of the non-terminal repeating units of the polymer are isobutylene units and containing at least one group having the formula

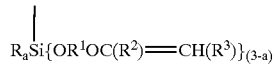

wherein R is independently selected from the group consisting of monovalent hydrocarbon groups and alkoxy groups, $R^1$ is a divalent hydrocarbon group having from 2 to 20 carbon atoms, $R^2$ and $R^3$ are independently selected from the group consisting of a hydrogen atom and a monovalent hydrocarbon group, and a has a value of 0 to 2;
(B) a cationic photoinitiator; and
(C) a free radical photoinitiator.

23. A method of making an article of manufacture comprising:
(I) applying a radiation curable composition comprising:
(A) an alkenyl ether-functional polyisobutylene polymer in which at least 50 mole percent of the non-terminal repeating units of the polymer are isobutylene units and containing at least one group having the formula

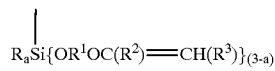

wherein R is independently selected from the group consisting of monovalent hydrocarbon groups and alkoxy groups, $R^1$ is a divalent hydrocarbon group having from 2 to 20 carbon atoms, $R^2$ and $R^3$ are independently selected from the group consisting of a hydrogen atom and a monovalent hydrocarbon group, and a has a value of 0 to 2;
(B) a cationic photoinitiator; and
(C) a free radical photoinitiator to a solid substrate to form a coating; and
(II) exposing the coating to an energy source selected from the group consisting of (i) ultraviolet light and (ii) visible light in an amount sufficient to cure the coating.

24. A method according to claim 23, wherein the composition further comprises (D) an alkenyl ether compound which is free of isobutylene units.

25. A method according to claim 23, wherein the radiation curable composition further comprises (E) an alkylphenol having from 6 to 18 carbon atoms.

26. A method according to claim 24, wherein the radiation curable composition further comprises (E) an alkylphenol having from 6 to 18 carbon atoms.

27. A method according to claim 23, wherein the solid substrate is glass.

28. A hydrocarbon silicone alkenyl ether compound having the formula

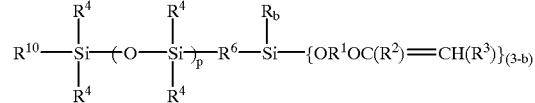

wherein $R^1$ and $R^6$ are divalent hydrocarbon groups having from 1 to 20 carbon atoms, $R^4$ is a monovalent hydrocarbon group having from 1 to 20 carbon atoms, $R^{10}$ is an alkyl group having from 8 to 16 carbon atoms, $R^2$ and $R^3$ are independently selected from a group consisting of a hydrogen atom and a monovalent hydrocarbon group, R is independently selected from the group consisting of $R^4$ and an alkoxy group, b has a value of 0 to 2, and p has a value of 0 to 1.

29. A compound according to claim 28, wherein $R^1$ is butylene, $R^6$ is ethylene, $R^4$ is methyl, $R^2$ and $R^3$ are each hydrogen atoms, $R^{10}$ is selected from the group consisting of dodecyl and hexadecyl, R is independently selected from the group consisting of methyl and methoxy, b has a value of 0, and p has a value of 1.

30. A hydrocarbon silicone alkenyl ether compound having the formula

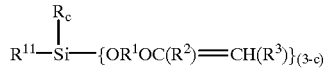

wherein R is independently selected from a group consisting of monovalent hydrocarbon group having from 1 to 20 carbon atoms and an alkoxy group, $R^2$ and $R^3$ are independently selected from group consisting of a hydrogen atom and a monovalent hydrocarbon group, $R^{11}$ is an alkyl group having from 8 to 16 carbon atoms, $R^1$ is a divalent hydrocarbon group having 1 to 20 carbon atom and c has a value of 0 to 2.

31. A compound according to claim 30, wherein $R^1$ is butylene, $R^2$ and $R^3$ are each hydrogen atoms, R is independently selected from the group consisting of methyl and methoxy, $R^{11}$ is selected from the group consisting of dodecyl and hexadecyl, and c has a value of 0.

* * * * *